(12) United States Patent
Okihara

(10) Patent No.: US 9,387,150 B2
(45) Date of Patent: Jul. 12, 2016

(54) INTEGRATED PUNCTURE NEEDLE ADAPTER

(75) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 87 days.

(21) Appl. No.: 14/005,110

(22) PCT Filed: Mar. 13, 2012

(86) PCT No.: PCT/JP2012/056343
§ 371 (c)(1),
(2), (4) Date: Sep. 13, 2013

(87) PCT Pub. No.: WO2012/128115
PCT Pub. Date: Sep. 27, 2012

(65) Prior Publication Data
US 2014/0005598 A1    Jan. 2, 2014

(30) Foreign Application Priority Data

Mar. 18, 2011 (JP) ................... 2011-061507

(51) Int. Cl.
*A61J 1/20* (2006.01)
*A61M 5/158* (2006.01)

(52) U.S. Cl.
CPC ............... *A61J 1/2096* (2013.01); *A61M 5/158* (2013.01); *A61J 1/201* (2015.05)

(58) Field of Classification Search
CPC ........ A61M 5/158; A61J 1/2096; A61J 1/201
USPC ............................................. 604/264, 85, 87
See application file for complete search history.

(56) References Cited

U.S. PATENT DOCUMENTS

| | | | |
|---|---|---|---|
| 3,796,218 A * | 3/1974 | Burke et al. | ................... 604/411 |
| 4,657,535 A | 4/1987 | Nishimura | |
| 4,969,876 A | 11/1990 | Patterson | |
| 5,344,417 A | 9/1994 | Wadsworth, Jr. | |
| 5,832,971 A | 11/1998 | Yale et al. | |
| 5,887,633 A | 3/1999 | Yale et al. | |

(Continued)

FOREIGN PATENT DOCUMENTS

| | | |
|---|---|---|
| EP | 0587347 | 3/1994 |
| JP | 60-241452 | 11/1985 |

(Continued)

OTHER PUBLICATIONS

EPO Search Report dated Nov. 25, 2013.

(Continued)

*Primary Examiner* — Theodore Stigell
(74) *Attorney, Agent, or Firm* — Greenblum & Bernstein P.L.C.

(57) ABSTRACT

The integrated puncture needle adapter is equipped with: a puncture needle; a needle hub; a tubular fixing part for fixing the needle hub; a tubular puncture needle accommodating part provided on a distal side of the tubular fixing part and having therein an accommodating space for accommodating the puncture needle; a second connecting part provided on a distal side of the puncture needle accommodating part; and a separable part which is formed between the tubular fixing part and the puncture needle accommodating part. A part on the distal side of the separable part is separable from a part on the proximal side of the separable part. The puncture needle is exposed when separated.

14 Claims, 9 Drawing Sheets

(56) References Cited

U.S. PATENT DOCUMENTS

| | | |
|---|---|---|
| 2004/0122374 A1 | 6/2004 | Hasegawa |
| 2010/0204679 A1 | 8/2010 | Denenburg |

FOREIGN PATENT DOCUMENTS

| | | | |
|---|---|---|---|
| JP | 61-257654 | | 11/1986 |
| JP | 10-57503 | | 3/1998 |
| JP | 2001-327599 | | 11/2001 |
| JP | 2004-194953 | | 7/2004 |
| JP | 2005-143677 | * | 6/2005 |
| JP | 3123361 | | 7/2006 |
| JP | 2010-538744 | | 12/2010 |

OTHER PUBLICATIONS

International Search report dated Apr. 24, 2012.
China Office action, dated Apr. 17, 2014 along with an English translation thereof.

* cited by examiner

INTEGRATED PUNCTURE NEEDLE ADAPTER

TECHNICAL FIELD

The present invention relates to an integrated puncture needle adapter.

BACKGROUND ART

For example in the case where a patient self-injects a drug solution such as a blood preparation, a drug may be dissolved or diluted with a liquid, and the resulting drug solution may be used by sucking it with a syringe. These operations are carried out in the following manner (see, for example, Patent Document 1).

First, an adapter for connecting the syringe storing the liquid therein is attached to a drug container storing the drug therein, and the drug container and the syringe are interconnected through the adapter. Next, the syringe is operated to transfer the liquid in the syringe into the drug container, and to dissolve the drug in the liquid, thereby obtaining the drug solution. Subsequently, the syringe is operated to suck the drug solution in the drug container into the syringe so that the drug solution is filled into the syringe. Next, the adapter is detached from the syringe, an injection needle is attached to the syringe in place of the adapter, the injection needle is made to puncture a living body, and the drug solution in the syringe is administered into the living body.

However, the conventional procedure in which the adapter and the syringe are thus used has the following problems. The adapter and the injection needle should be replaced with each other to the syringe at the time of dissolving the drug and at the time of administering the drug solution. Thus, the process is troublesome, and there is a risk of misuse. In addition, at the time of change-over of the adapter and the injection needle, there may arise problems of leakage of the drug solution in the syringe, and contamination of the drug solution due to contamination of a distal end of the syringe. Further, priming of the inside of the injection needle is needed at the time of administering the drug solution, which is bothersome.

Patent Document 1: Japanese Patent Laid-open No. 2004-194953

DISCLOSURE OF INVENTION

It is an object of the present invention to provide an integrated puncture needle adapter capable of exhibiting excellent operability while preventing contamination of a drug solution.

In order to attain the above object, according to the present invention, there is provided an integrated puncture needle adapter for connecting a drug storage container having a drug storage space to store a drug and a liquid storage container having a liquid storage space to store a liquid for dissolving or diluting the drug, the integrated puncture needle adapter including:

a puncture needle having a needle tip capable of puncturing a living body at a distal end of the puncture needle and an internal passage opening at both ends of the puncture needle;

a needle hub which supports the puncture needle so that the needle tip of the puncture needle protrudes from a distal side of the needle hub;

a first connecting part which is provided on a proximal side of the needle hub, and which connects the liquid storage space and the internal passage in a liquid-tight manner by a connection with the liquid storage container;

a tubular fixing part which is provided on the distal side of the needle hub, and which fixes the needle hub;

a tubular puncture needle accommodating part which is provided on a distal side of the tubular fixing part integrally with the tubular fixing part, and wherein the tubular puncture needle accommodating part has therein an accommodating space for accommodating the puncture needle;

a second connecting part which is provided on a distal side of the puncture needle accommodating part so as to communicate with the accommodating space, and wherein the second connecting part connects the drug storage space and the internal passage in a liquid-tight manner by a connection with the drug storage container; and a separable part formed between the tubular fixing part and the puncture needle accommodating part, wherein the separable part is capable of separating a distal part at a distal side relative to the separable part from a proximal part at a proximal side relative to the separable part, and the puncture needle is exposed when separated.

In the integrated puncture needle adapter of the present invention, preferably, the liquid storage container is a syringe, and the integrated puncture needle adapter is used by, in a state where the drug storage container is connected to the second connecting part and the syringe is connected to the first connecting part, transferring the liquid into the drug storage space through the puncture needle, the accommodating space and the second connecting part by an operation of the syringe to obtain a drug solution as a mixture of the liquid with the drug;

sucking the drug solution into the syringe through the second connecting part, the accommodating space and the puncture needle by the operation of the syringe; and separating the distal part at the distal side relative to the separable part together with the drug storage container from the proximal part at the proximal side relative to the separable part, thereby exposing the puncture needle.

In the integrated puncture needle adapter of the present invention, preferably, the separable part is comprised of an easy-to-break part which is easier to break than parts other than the separable part.

In the integrated puncture needle adapter of the present invention, preferably, the easy-to-break part is broken by rotating at least one of a distal part at a distal side relative to the easy-to-break part and a proximal part at a proximal side relative to the easy-to-break part in a circumferential direction in relation to the other.

In the integrated puncture needle adapter of the present invention, preferably, the puncture needle accommodating part is provided with a projected part which is projected outward.

In the integrated puncture needle adapter of the present invention, preferably, the needle hub is provided with a projected part which is projected outward.

BEST MODE FOR CARRYING OUT THE INVENTION

Now, an integrated puncture needle adapter according to the present invention will be described in detail below, based on its preferred embodiments shown in the accompanying drawings.

First Embodiment

First, a first embodiment of the integrated puncture needle adapter of the present invention will be described.

Figure 1:
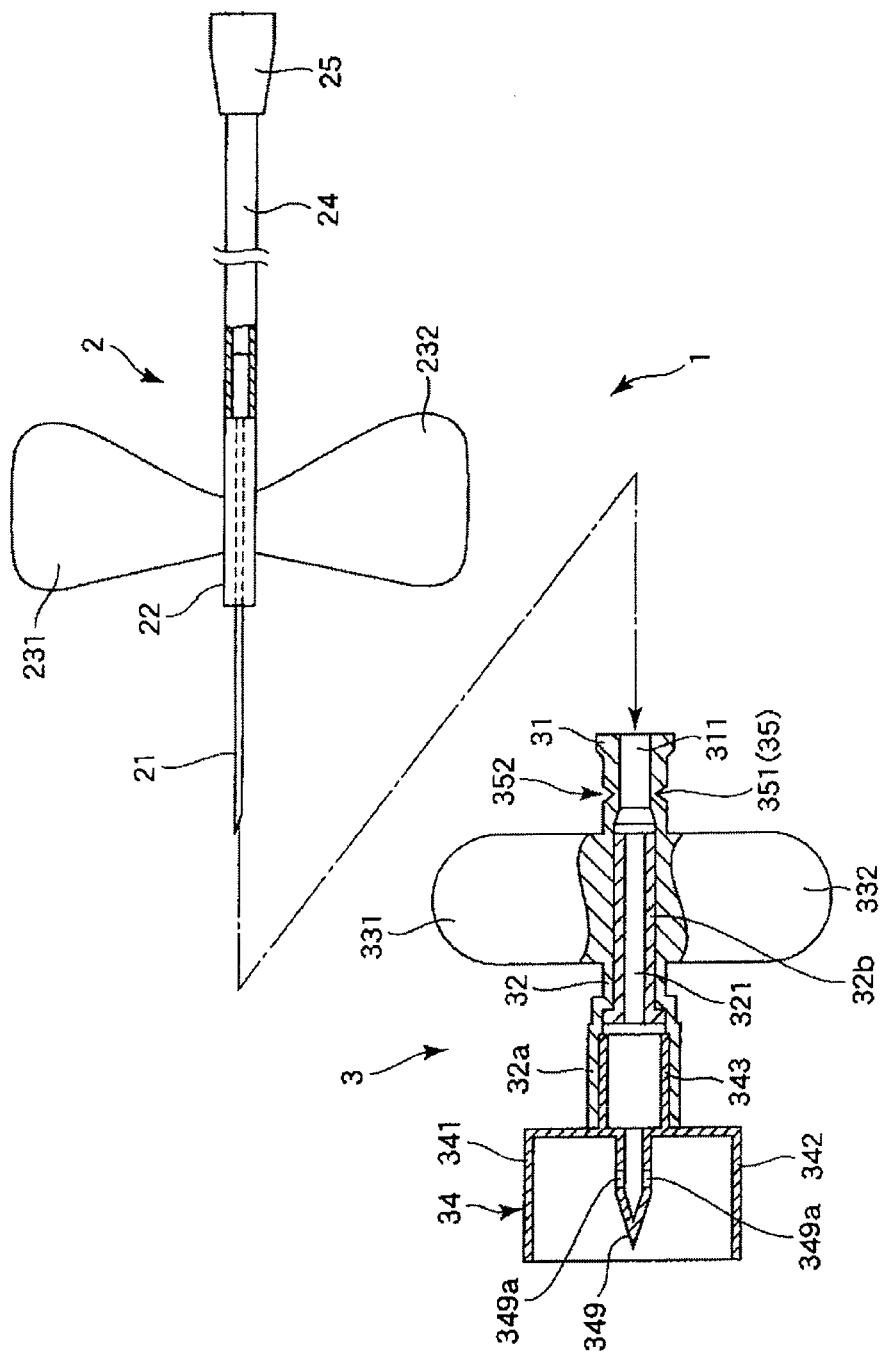
FIG. 1 is a disassembly drawing (longitudinal sectional view) showing a first embodiment of an integrated puncture needle adapter of the present invention.
Figure 2:
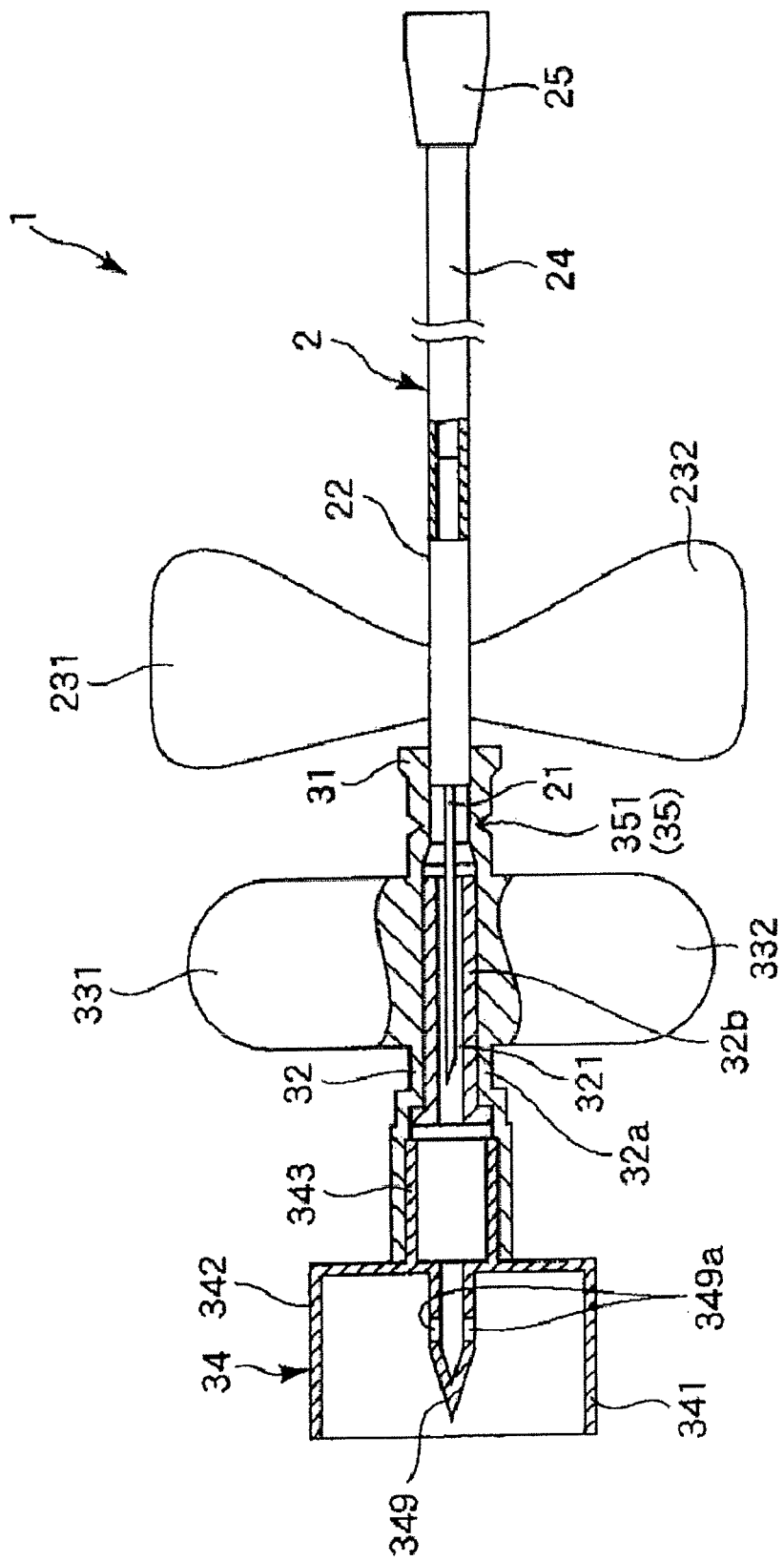
FIG. 2 is an assembly drawing (longitudinal sectional view) of the integrated puncture needle adapter shown in FIG. 1.
Figure 3:
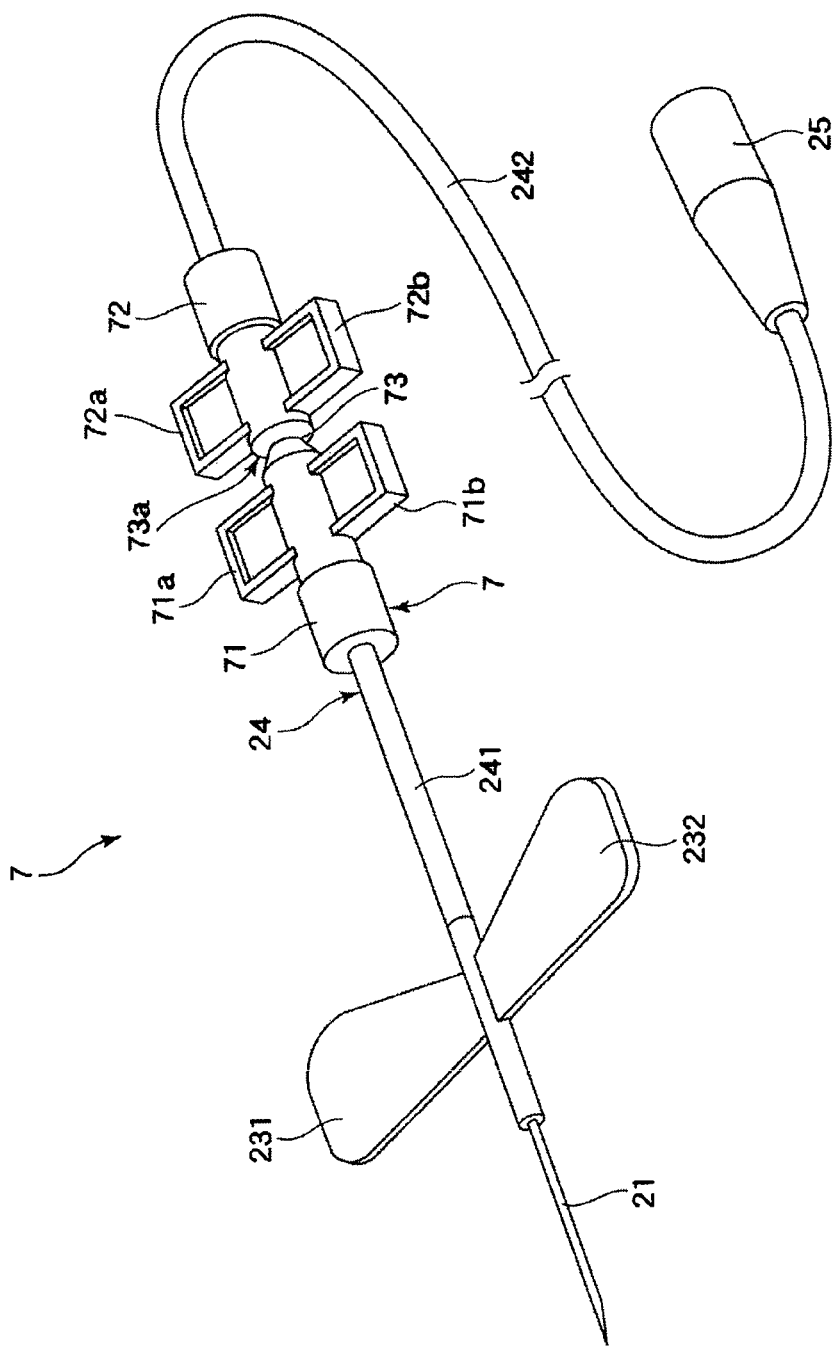
FIG. 3 is a perspective view of a winged needle possessed by the integrated puncture needle adapter shown in FIG. 1.
Figure 4:
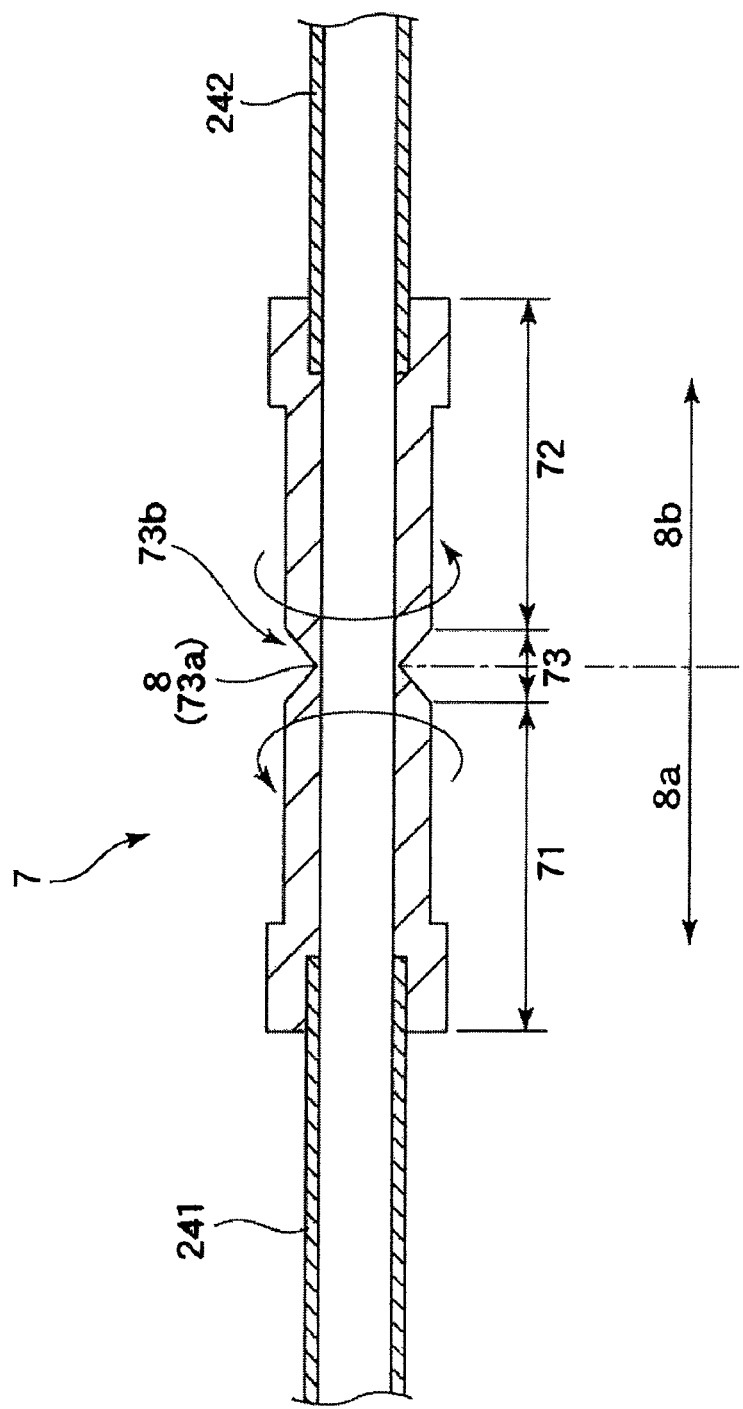
FIG. 4 is a sectional view of a tube possessed by the winged needle shown in FIG. 3.

FIG. 1 is a disassembly drawing (longitudinal sectional view) showing the first embodiment of an integrated puncture needle adapter of the present invention; FIG. 2 is an assembly drawing (longitudinal sectional view) of the integrated puncture needle adapter shown in FIG. 1; FIG. 3 is a perspective view of a winged needle possessed by the integrated puncture needle adapter shown in FIG. 1; FIG. 4 is a sectional view of a tube possessed by the winged needle shown in FIG. 3; and FIGS. 5 to 8 are views for illustrating a procedure of using the integrated puncture needle adapter shown in FIG. 1. Incidentally, for convenience of description, the left side in each of FIGS. 1 to 4 will be referred to as "distal side", and the right side as "proximal side", while the lower side in FIGS. 5 to 8 will be referred to as "distal side", and the upper side as "proximal side".

The integrated puncture needle adapter 1 shown in FIG. 1 includes a winged needle 2 and an adapter 3, and is configured by combining these members as shown in FIG. 2. Now, the winged needle 2 and the adapter 3 will be sequentially described in detail below.

Winged Needle

As shown in FIGS. 1 and 2, the winged needle 2 is composed of: a puncture needle 21 having an internal passage opening at both ends thereof; a needle hub 22 which supports and fixes the puncture needle 21; a pair of wings (projected parts) 231 and 232 provided on the needle hub 22; a tube 24 connected to a proximal portion of the needle hub 22; and a first connecting part 25 connected to a proximal portion of the tube 24.

The puncture needle 21 is provided at a distal end thereof with a needle tip capable of puncturing a living body. With the needle tip made to puncture the living body, a drug solution 300 which will be described later can be injected (administered) into the living body.

As the puncture needle 21 configured as above, there is preferably used a needle of a size of 18 to 33 G (outside diameter: 0.2 to 0.45 mm) according to the ISO medical needle tube standard (ISO 9626: 1991/Amd. 1: 2001 (E)), more preferably a needle of a size of 21 to 25 G.

In addition, a material constituting the puncture needle 21 is not specifically restricted. Examples of the material applicable here include various metallic materials such as stainless steel, aluminum, aluminum alloys, titanium, titanium alloys, super-elastic alloys such as Ni—Ti alloys, etc. and various rigid resin materials such as polyphenylene sulfide.

To an outer circumference of a proximal portion of the puncture needle 21 as above, the needle hub 22 which is hollow cylindrical in shape is secured in a liquid-tight manner. This results in that the puncture needle 21 is supported on and fixed to the needle hub 22. Of the needle hub 22, the proximal portion is reduced in diameter as compared with a distal portion, and the proximal portion is fitted in the tube 24, whereby the needle hub 22 and the tube 24 are interconnected. This results in that the puncture needle 21 and the tube 24 are interconnected.

The needle hub 22 as above is provided with the pair of wings 231 and 232 which project in opposite directions each other. In the present embodiment, the wings 231 and 232 have their base portions joined to each other to form a single flat plate-shaped body, onto which the needle hub 22 is joined. In addition, the wings 231 and 232 are flexible, and are so configured that they can be opened and closed when they are bent or curved near base end portions thereof.

The wings 231 and 232 as above have the following functions. At the time of puncturing the living body by the puncture needle 21, the wings 231 and 232 are picked up in the manner of folding them, and the puncture needle 21 is made to puncture the living body. After the puncturing, the wings 231 and 232 are opened, and they are fixed to the skin by use of a pressure sensitive adhesive tape or the like, whereby the puncture needle 21 can be fixed to the living body. Thus, the provision of the wings 231 and 232 ensures that the puncture of the living body by the puncture needle 21 can be carried out easily and smoothly, and the puncture needle 21 can be fixed to the living body easily and assuredly.

Incidentally, the wings 231 and 232 can be formed integrally with the needle hub 22.

In addition, to the proximal side of the needle hub 22, the tube 24 which is flexible and serves as a flow path for a liquid 100 or a drug solution 300 to be described later is connected in a liquid-tight manner. A lumen of the tube 24 communicates, in a liquid-tight manner, with the internal passage of the puncture needle 21.

Incidentally, while the length of the tube 24 is not particularly limited, it is preferably about 15 to 40 cm, more preferably about 20 to 30 cm. Such a setting ensures that the length of the tube 24 is suited to self-injection as in the using method described later, so that the self-injection can be carried out more easily.

Incidentally, materials constituting the needle hub 22, the wings 231 and 232 and the tube 24 are each not particularly restricted. Examples of the materials applicable here include polyolefins such as polyethylene, polypropylene, an ethylene-vinyl acetate copolymer, etc., polyvinyl chloride, polybutadiene, polyamides, and polyesters. Incidentally, these components are each preferably formed from a transparent or semi-transparent material, for securing visibility of the inside thereof.

On the proximal side of the tube 24 is provided the first connecting part 25, for connection with a syringe (liquid storage container) 500 which will be described later. The first connecting part 25 as above is formed therein with an inner cavity (not shown), through which the inside of the syringe 500 (liquid storage space) and the lumen of the tube 24 can be interconnected in a liquid-tight manner. This results in that the inside of the syringe 500 (the liquid storage space) and the internal passage of the puncture needle 21 communicate with each other in a liquid-tight manner.

Incidentally, to the first connecting part 25 as above, a filter having a filter member which is permeable to gases but does not permits bacteria to pass therethrough may be detachably mounted, until the time of connection of the syringe. Incidentally, examples of a constituent material of the filter member include nonwoven fabrics and papers of polypropylene, polysulfone, regenerated cellulose, polyamides, polyesters, polyethylenes, polytetrafluoroethylene, etc., which may or may not have undergone a filling-up treatment.

In addition, an easy-to-break part 8 is formed at an intermediate portion of the tube 24. Such an easy-to-break part 8 is configured to be easier to break as compared with parts other than it, specifically, a part immediately on a distal side thereof and a part immediately on a proximal side thereof.

By breakage of such an easy-to-break part 8, the winged needle 2 can be separated into a first part 8a located on the distal side of the easy-to-break part 8 and including the puncture needle 21 and a second part 8b located on the proximal side of the easy-to-break part 8.

Wastes including the puncture needle 21 should be treated as a "needle waste" appropriately in conformity with relevant laws and regulations. Thus, the separation into the first part 8a inclusive of the puncture needle 21 and the second part 8b as the rest, as in the case of the winged needle 2, ensures that it suffices to dispose of only the first part 8a as the needle waste, so that an amount of the needle waste generated is reduced. This results in enhanced economy in discarding the winged needle 2. In other words, the frequency of disposal of wastes as the needle waste can be lowered, and expenditure on waste disposal can be suppressed. Since the separation into the first part 8a and the second part 8b can be easily achieved by the breakage of the easy-to-break part 8, the winged needle 2 is free of bother in discarding thereof and, hence, excellent in operability.

Now, the easy-to-break part 8 will be described in detail below.

As shown in FIGS. 3 and 4, the tube 24 includes: a distal-side tube 241 connected at its distal portion to the needle hub 22; a proximal-side tube 242 located on the proximal side relative to the distal-side tube 241 and connected at its proximal portion to the first connecting part 25; and a tubular interconnection member 7 for interconnecting the distal-side tube 241 and the proximal-side tube 242.

In addition, the interconnection member 7 includes: a distal portion 71 connected to the distal-side tube 241; a proximal portion 72 connected to the proximal-side tube 242; and an intermediate portion 73 which interconnects the distal portion 71 and the proximal portion 72.

The distal portion 71 is formed with a pair of handles 71a and 71b projecting on both sides thereof, and the proximal portion 72 is formed with a pair of handles 72a and 72b projecting on both sides thereof. These handles 71a, 71b, 72a and 72b are each flat plate-like in shape. In addition, each of the handles 71a, 71b, 72a and 72b has a structure wherein both major surfaces thereof are recessed, exclusive of edge portions, so as to ensure easy hooking of fingers on the handles.

The intermediate portion 73 has a thin-walled part 73a thinner than the distal portion 71 and the proximal portion 72, and the thin-walled part 73a constitutes the easy-to-break part 8. As the thin-walled part 73a is made to be thinner than the distal portion 71 and the proximal portion 72, it is more brittle and is broken by a weaker force, as compared with the distal portion 71 and the proximal portion 72. With the easy-to-break part 8 composed of such a thin-walled part 73a, therefore, it is possible to form the easy-to-break part 8 which can exhibit its function reliably and is simple in configuration.

While description will be made in connection with the using procedure later, the easy-to-break part 8 is used, for example, as follows. With the distal part 71 gripped by one hand and with the proximal part 72 gripped by the other hand, at least one of the distal portion 71 and the proximal portion 72 is rotated in the manner of twisting it relative to the other, whereby the easy-to-break part 8 is broken in the manner of being twisted (wrenched) off. By such a method, the easy-to-break part 8 can be broken easily. Incidentally, the just-mentioned procedure will hereinafter be referred to also as "breaking procedure", for convenience of the description.

Specifically, in the present embodiment, the distal portion 71 is formed with the pair of handles 71a and 71b, and the proximal portion 72 is formed with the pair of handles 72a and 72b. With the fingers hooked on these handles 71a, 71b, 72a and 72b, it becomes easier to grip the distal portion 71 and the proximal portion 72, and also to rotate the distal portion 71 and the proximal portion 72. Consequently, the above-mentioned breaking procedure can be carried out more easily and smoothly.

In addition, the thin-walled part 73a (the easy-to-break part 8) is preferably flexible (pliable), specifically, stretchable or expandable-and-contractible. This ensures that in the case of carrying out the above-mentioned breaking procedure, as a relative rotating angle of the distal portion 71 and the proximal portion 72 increases, the easy-to-break part 8 is deformed in the manner of being extended. Then, when the rotating angle exceeds a predetermined angle, the limit of the extension is exceeded, whereby the easy-to-break part 8 is broken in the manner of being twisted (wrenched) off.

Such a configuration ensures that the liquid-tightness inside the tube 24 can be secured until immediately before the breakage, in other words, during the course of deformation of the easy-to-break part 8. Therefore, for example in the state where the easy-to-break part 8 is not broken despite unintentional deformation of the easy-to-break part 8, the liquid-tightness inside the tube 24 is being maintained; therefore, contamination of the inside of the tube 24, leakage of liquid from the tube 24 and the like troubles can be prevented from occurring.

Incidentally, the above-mentioned predetermined angle is preferably not less than 45 degrees, more preferably not less than 90 degrees. This ensures that the easy-to-break part 8 is not broken by some extent of rotation. Consequently, unwilling breakage or unintended breakage of the easy-to-break part 8 can be effectively prevented from taking place.

Besides, the easy-to-break part 8 is preferably provided at the intermediate portion of the tube 24, and an area within the range of 10 cm, more preferably within the range of 3 to 6 cm, from the proximal end of the needle hub 22. This makes it possible to further reduce the volume (bulkiness) of the first part 8a, and to further suppress the amount of the needle waste generated. Particularly, where the distance from the proximal end of the needle hub 22 to the easy-to-break part 8 is set to be 3 to 6 cm, not only the above-mentioned effect can be exhibited but also the easy-to-break part 8 can be set to appropriately distant from the puncture needle 21, so that the operability of the puncture needle 21 is not spoiled.

The thin-walled part 73a (the easy-to-break part 8) is formed by forming a groove 73b, roughly V-shaped in cross section, in an outer circumference of the intermediate portion 73. This ensures that the thin-walled part 73a (the easy-to-break part 8) can be easily formed, and that the groove 73b serves as a mark which permits the user to easily confirm visually the easy-to-break part 8. As a result, the above-mentioned breaking procedure can be carried out easily, and the operability is enhanced.

Incidentally, the groove 73b is so formed as not to penetrate to the inside of the interconnection member 7 (the lumen of the tube 24); by this structure, the liquid-tightness of the tube 24 is secured. In addition, the cross-sectional shape of the groove 73b is not restricted to the V-shape, and it may be semi-circle, for example.

Such a groove 73b is preferably formed over the whole circumference of the intermediate portion 73. In other words, the groove 73b is preferably ring-like in shape. This ensures that the easy-to-break part 8 can be formed along the whole circumference of the intermediate portion 73. Consequently, the easy-to-break part 8 has a configuration suited to the act of twisting (wrenching) it off following the above-mentioned breaking procedure, and the breaking operation can be carried out easily and assuredly.

A thickness of the thin-walled part 73a (the easy-to-break part 8) as above, which may vary depending on a material constituting the interconnection member 7 and the like factors, is preferably about 0.2 to 1.0 mm, more preferably about 0.3 to 0.5 mm, at a position corresponding to a bottom of the groove 73b. This ensures that the easy-to-break part 8 has an appropriate degree of mechanical strength. Consequently, it is possible to effectively avoid situations in which the easy-to-break part 8 is so excessively brittle as to bring about unwilling unintended breakage thereof during use and, on the contrary, the easy-to-break part 8 is so excessively tough as to require a large force for breakage thereof.

Specifically, setting the thickness of the thin-walled part 73a to the above-mentioned value ensures the following. In the case where there is no will to break the easy-to-break part 8, such as during use of the instrument, the breakage can be securely prevented from taking place. In the case where there is a will to break the easy-to-break part 8, such as at the time of discarding the instrument after use, the breakage can be easily achieved.

While the distal portion 71, the proximal portion 72 and the intermediate portion 73 have been described above, these components are formed integrally. Examples of materials constituting these components, namely the material constituting the interconnection member 7, include various resins such as polyvinyl chloride, polyethylene, polypropylene, and polyamides.

Adapter

As shown in FIGS. 1 and 2, the adapter 3 is composed of: a tubular fixing part 31 fixed to the needle hub 22; a puncture needle accommodating part 32 provided on a distal side of the tubular fixing part 31; a pair of wings 331 and 332 provided on the puncture needle accommodating part 32; a second connecting part 34 provided on a distal side of the puncture needle accommodating part 32; and a separable part 35 provided between the tubular fixing part 31 and the puncture needle accommodating part 32.

Puncture Needle Accommodating Part

The puncture needle accommodating part 32 is tubular in shape, and has an accommodating space 321 therein. In the condition where the adapter 3 is fixed to the winged needle 2, as shown in FIG. 2, the puncture needle 21 is accommodated in the accommodating space 321. This ensures that the puncture needle 21 is protected by the adapter 3, whereby the breakage of the puncture needle 21 and the contamination of the puncture needle 21 can be prevented.

The accommodating space 321 is preferably so configured that its inside diameter is greater than the outside diameter of the puncture needle 21, and, hence, the puncture needle 21 can be accommodated therein in a non-contact state. As a result, the puncture needle 21 can be effectively prevented from being broken or marred due to contact with an inner wall of the puncture needle accommodating part 32 (namely, a wall surface defining the accommodating space 321). In addition, even if the puncture needle accommodating part 32 is somewhat deformed by an external force, the puncture needle 21 inside is not deformed. In this point, also, the puncture needle 21 can be effectively prevented from being broken or marred.

In addition, while a diameter of the accommodating space 321 is not particularly limited, the diameter is preferably greater by about 0.2 to 5 mm than the outside diameter of the puncture needle 21. Such a sizing ensures that the non-contact state between the inner wall of the puncture needle accommodating part 32 and the puncture needle 21 can be secured sufficiently, and, further, the volume of the accommodating space 321 can be reduced. With the volume of the accommodating space 321 reduced, it is possible to reduce the amount of the drug solution 300 left in the accommodating space 321 when the instrument is used as will be described later. Accordingly, the drug solution 300 can be used efficiently.

In the present embodiment, the puncture needle accommodating part 32 includes: a main body 32a having an inner cavity opening on the distal side; and a tubular hard portion 32b provided inside the inner cavity of the main body 32a. An internal space of the hard portion 32b constitutes the accommodating space 321.

The hard portion 32b is fixed to an inner surface of the main body 32a by, for example, fitting, adhesion or the like. Besides, an inner circumferential surface of the main body 32a and an outer circumferential surface of the hard portion 32b are each formed with a stepped part. The stepped part of the hard portion 32b makes contact with the stepped part of the main body 32a, whereby the hard portion 32b is positioned relative to the main body 32a.

Due to the hard portion 32b thus provided inside, the puncture needle accommodating part 32 is enhanced in overall strength thereof and is restrained from deformation. Therefore, the puncture needle accommodating part 32 can protect more effectively the puncture needle 21 accommodated therein. In addition, since strength is maintained sufficiently by the hard portion 32b, a degree of freedom in design of the main body 32a is increased. As a result, it becomes easy, for example, to form the main body 32a integrally with the tubular fixing part 31, as will be described later.

Examples of a material constituting the hard portion 32b include: various resins such as polyvinyl chloride, polyethylene, polypropylene, cyclic polyolefins, polystyrene, poly-(4-methylpentene-1), polycarbonate, acrylic resins, an acrylonitrile-butadiene-styrene copolymer, polyesters such as polyethylene terephthalate, polyethylene naphthalate, etc., a butadiene-styrene copolymer, polyamides (e.g., nylon 6, nylon 6-6, nylon 6-10, nylon 12), and various metallic materials such as stainless steel, aluminum, aluminum alloys, etc.

Wing

The puncture needle accommodating part 32 is provided with the pair of wings (projected parts) 331 and 332 projected to opposite directions each other. The wings 331 and 332 are each flat plate-like in shape. In addition, the wings 331 and 332 are preferably configured to be comparatively hard and be difficult to deform. The wings 331 and 332 function as handles on which to hook fingers. With the fingers hooked on the wings 331 and 332, it becomes easy to rotate the puncture needle accommodating part 32 in the circumferential direction thereof. Consequently, operability of the adapter 3 is enhanced, as will be described later in connection with the using method.

Incidentally, the shape of each of the wings 331 and 332 is not specifically restricted insofar as the above-mentioned function as a handle can be exhibited. Besides, for example, one of the wings 331 and 332 may be omitted.

Tubular Fixing Part

The tubular fixing part 31, tubular in shape, is provided on a proximal side of the puncture needle accommodating part 32. The tubular fixing part 31 has a function of connecting and fixing the adapter 3 to the winged needle 2. The tubular fixing part 31 as above has an opening 311 which opens to a proximal side. The opening 311 is slightly smaller than the needle hub 22 in diameter. With the needle hub 22 fitted into the opening 311, the tubular fixing part 31 is fixed to the needle hub 22 in a liquid-tight manner.

Incidentally, a method of fixing the tubular fixing part 31 and the needle hub 22 to each other is not restricted to the above-mentioned fitting; the fixation may be effected by use of an adhesive or by welding, or by a combination of them. Particularly when the fixation is effected by use of an adhesive or by welding, the tubular fixing part 31 and the needle hub 22 can be fixed more firmly. Consequently, it is possible to securely prevent the tubular fixing part 31 from being disengaged from the needle hub 22, at the time of twisting (wrenching) off the separable part 35 (easy-to-break part 351), as will be described later.

In addition, the opening 311 communicates, on the distal side thereof, with the accommodating space 321 so as to permit the passage therethrough of the puncture needle 21. In the state where the tubular fixing part 31 is fixed to the needle hub 22, the puncture needle 21 is accommodated in the accommodating space 321.

Separable Part

Between the puncture needle accommodating part 32 and the tubular fixing part 31 is formed the separable part 35. In the adapter 3, with the separable part 35 as a boundary, a part on a proximal side thereof and a part on a distal side thereof are separable from each other. In other words, the tubular fixing part 31 and the puncture needle accommodating part 32 can be separated from each other.

The separable part 35 is composed of the easy-to-break part 351 which is easily broken by a smaller force (torque) as compared with parts other than it. The easy-to-break part 351 is set to be thinner (in wall thickness) and more brittle than the parts. Specifically, between the puncture needle accommodating part 32 and the tubular fixing part 31, a groove 352 which is V-shaped in cross section and opening in an outer circumferential surface is formed over the whole circumference, thereby forming a thinner and more brittle part, namely, the easy-to-break part 351. In this way, the easy-to-break part 351 can be formed easily.

A wall thickness of the easy-to-break part 351, which may vary depending on a material constituting this part, is for example preferably 0.1 to 1.0 mm, more preferably 0.2 to 0.5 mm.

The easy-to-break part 351 is broken in the manner of being twisted (wrenched) off, for example, by rotating at least one of the tubular fixing part 31 and the puncture needle accommodating part 32 relative to the other by not less than a predetermined angle; as a result, the puncture needle accommodating part 32 and the tubular fixing part 31 are separated from each other.

Specifically, as the rotating angle increases, the easy-to-break part 351 is deformed in the manner of being extended. When the predetermined angle is exceeded, the limit of the extension is exceeded, attended by breakage of the easy-to-break part 351, whereby the puncture needle accommodating part 32 and the tubular fixing part 31 are separated from each other.

By twisting (wrenching) off the easy-to-break part 351 in the above-mentioned manner, the puncture needle accommodating part 32 and the tubular fixing part 31 can be separated from each other, without exerting any load on the puncture needle 21 accommodated in the puncture needle accommodating part 32. Therefore, the puncture needle 21 can be effectively prevented from undergoing deformation, breakage or the like.

The predetermined angle is preferably not less than 45 degrees, and more preferably not less than 90 degrees. This ensures that the easy-to-break part 351 is not broken by some extent of rotation. Therefore, it is possible to effectively prevent the easy-to-break part 351 from undergoing unwilling breakage or unintended breakage, so that misuse of the integrated puncture needle adapter 1 is prevented.

Incidentally, it is preferable that a damaged portion providing communication between the inside and the outside of the easy-to-break part 351, such as a through-hole, is not formed until immediately before the breakage of the easy-to-break part 351, namely during the course of deformation of the easy-to-break part 351. In other words, it is preferable that the liquid-tightness of the accommodating space 321 is maintained until the breakage of the easy-to-break part 351. This enables the liquid-tightness of the accommodating space 321 to be secured until the puncture needle accommodating part 32 is separated from the tubular fixing part 31. Consequently, unwilling contamination of the inside of the accommodating space 321, leakage of liquid from the accommodating space 321 and the like trouble can be prevented from occurring.

In addition, it is preferable for the easy-to-break part 351 to be located more to the proximal side, within the range from the distal end of the needle hub 22 to a needle tip of the puncture needle 21, in the state where the adapter 3 is fixed to the winged needle 2. In the present embodiment, the easy-to-break part 351 is located in the vicinity of the distal end of the needle hub 22. It is located at a proximal portion of the puncture needle 21. Such an arrangement ensures that that portion of the puncture needle 21 which is on the distal side relative to the distal end of the needle hub 22 can be substantially wholly exposed when the easy-to-break part 351 is twisted (wrenched) off to separate the puncture needle accommodating part 32 from the tubular fixing part 31. Consequently, the puncture of the living body by the puncture needle 21 can be carried out easily.

A material constituting the separable part 35 is preferably a flexible resin such as polyvinyl chloride, polyamides, polypropylene, and polyethylene. This permits the easy-to-break part 351 to be twisted (wrenched) off easily, as above-mentioned. Besides, the separable part 35, the tubular fixing part 31, and the puncture needle accommodating part 32 can be formed integrally.

Second Connecting Part

The second connecting part 34 is provided on the distal side of the puncture needle accommodating part 32. The second connecting part 34 has a function of connecting the adapter 3 with a vial (drug storage container) 600. Such a second connecting part 34 includes a main body portion 341, and a hollow needle (insertion part) 349 capable of puncturing a stopper 620 of the vial 600 which will be described later.

The main body portion 341 has a holder 342 having a bottomed tube-like shape which encircles the periphery of the hollow needle 349, and a tubular part 343 formed at a proximal portion of the holder 342 so as to project in the axial direction of the holder 342. The tubular part 343 is fixed to the puncture needle accommodating part 32 in a liquid-tight manner by fitting, welding, adhesion with an adhesive, or the like. As a result, the second connecting part 34 is fixed to the puncture needle accommodating part 32, and the tubular part 343 and the accommodating space 321 communicate with each other.

The hollow needle 349 is located inside the holder 342, and is formed at a bottom portion of the holder 342 so as to project in the axial direction of the holder 342. In addition, the hollow needle 349 is disposed at a position corresponding to the tubular part 343, and communicates with the accommodating space 321 through the tubular part 343. Besides, the hollow needle 349 is formed with holes 349a in a side portion of an intermediate part thereof, and the inside and the outside of the hollow needle 349 communicate with each other through the holes 349a. This ensures that when the hollow needle 349 punctures the stopper 620 of the vial (drug storage container) 600, the inside of the vial 600 (drug storage space) and the accommodating space 321 communicate with each other through the hollow needle 349, whereby the inside of the vial 600 (the drug storage space) and the internal passage of the puncture needle 21 communicate with each other in a liquid-tight manner.

Incidentally, a material constituting the second connecting part 34 is not specifically restricted. For instance, the same materials as those mentioned as examples of the material for the hard portion 32b above can be used.

In addition, before use, a cap for covering the hollow needle may be attached, in order to prevent contamination of the hollow needle 349. Besides, a liquid-permeable filter for removing foreign matters may be disposed between the hollow needle 349 and the accommodating space 321. This makes it possible to avoid a situation in which the drug left undissolved or undispersed in the inside of the vial 600 (the drug storage space) or debris of the stopper 620 of the vial (the drug storage container) 600 generated upon puncture of the stopper 620 by the hollow needle 349 or the like might be sucked in via the puncture needle 21. Consequently, a drug solution free of the foreign matters can be administered.

Thus, the integrated puncture needle adapter 1 and the adapter 3 have been described in detail above.

Now, the procedure (operation) of using the integrated puncture needle adapter 1 (the adapter 3) in performing self-injection will be described below, based on FIGS. 5 to 8.

[1] First, the adapter 3, the winged needle 2, the syringe (liquid storage container) 500 and the vial (drug storage container) 600 are prepared.

Incidentally, in the present embodiment, description will be made by taking the syringe 500 as an example of the liquid storage container, and the vial 600 as an example of the drug storage container. The syringe 500 includes a barrel (outer tube) 510, a gasket 520 slidable within the barrel 510, and a pusher (plunger) 530 operated to move the gasket 520 in the axial direction (longitudinal direction) of the barrel 510. In addition, the gasket 520 is connected to the distal end of the pusher 530.

A liquid 100 for dissolving or diluting a drug 200 stored in the vial 600 is sealed in a space defined by the barrel 510 and the gasket 520. The liquid 100 is not specifically restricted, and it is appropriately selected according to the drug 200. Examples of the liquid 100 include water for injection, a physiological saline, and glucose solutions. In addition, the sealing of the liquid 100 into the syringe 500 may be preliminarily performed; or, alternatively, the liquid 100 may be sucked into the syringe 500 before use.

The barrel 510 is composed of a member having a bottomed tube-like shape. At a distal portion, specifically at a central part of a distal-side bottom portion of the barrel 510, a mouth part 512 reduced in diameter as compared with a trunk part 511 of the barrel 510 is integrally and projectingly formed. Via the mouth part 512, the liquid 100 is discharged and a drug solution 300 is sucked in and discharged. In addition, the first connecting part 25 of the winged needle 2 is detachably connected to the mouth part 512.

On the other hand, the vial 600 includes a container body 610 storing the drug 200 therein, and a stopper 620 closing the opening of the container body 610. Gas-tightness of the inside of the container body 610 is maintained before use (during custody). In the drug storage container 600 as above, an internal space of the container body 610 constitutes a drug storage part 630 in which to store the drug 200.

The drug 200 is not specifically restricted. Examples of the drug 200 include blood preparations such as dried human blood coagulation factor VIII, etc., hormone preparations such as an insulin preparation, etc., and antivirotic agents such as an interferon preparation, etc.

In addition, the form of the drug 200 is not specifically restricted. Examples of the drug form include a solid form such as solid (tablet, granule, freeze-dried agent, etc.) and powder (powdery drug, etc.), and liquid (liquid drug, etc.).

Besides, a material constituting the container body 610 is not specifically restricted. Examples of the material include various glasses and various resins.

In addition, the stopper 620 is one that can be pierced through by the hollow needle 349 of the second connecting part 34. A material of the stopper 620 is not specifically restricted. Examples of the material include elastic materials such as various rubber materials and various thermoplastic elastomers.

Figure 5:
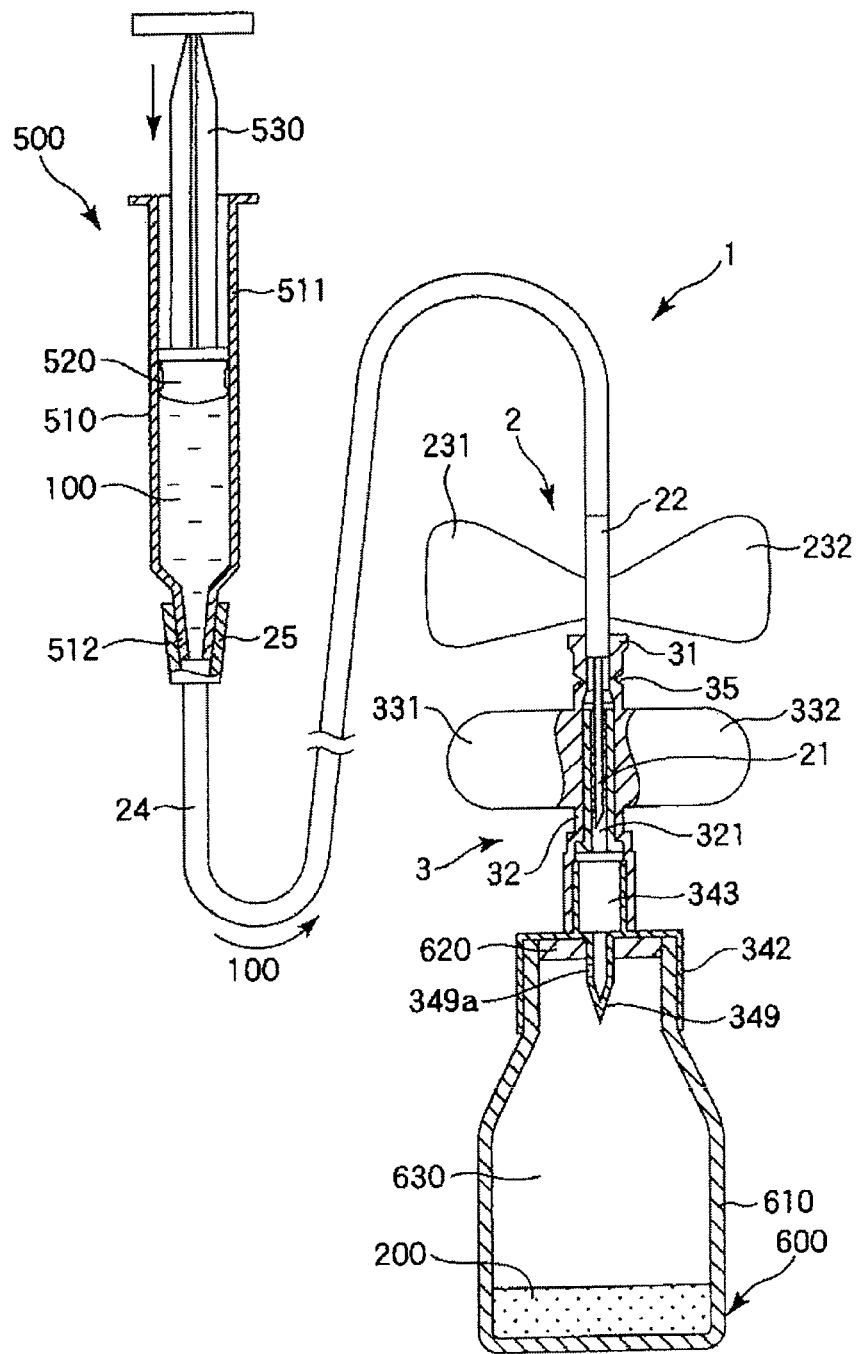
FIG. 5 is a view for illustrating a procedure of using the integrated puncture needle adapter shown in FIG. 1.

[2] Next, as shown in FIG. 5, the vial 600 is connected to the second connecting part 34 of the integrated puncture needle adapter 1 wherein the winged needle 2 and the adapter 3 are connected and fixed to each other as above-mentioned. In this instance, the vial 600 is pushed into the holder 342 of the second connecting part 34, starting from the side of the stopper 620 thereof. As a result, the hollow needle 349 of the second connecting part 34 pierces through the stopper 620 of the vial 600, so that the inside of the vial 600 (the drug storage part 630) and the accommodating space 321 communicate with each other through the hollow needle 349.

Incidentally, in the case where a negative pressure is present inside the vial 600, the above-mentioned filter is preferably mounted to the first connecting part 25 of the winged needle 2. This ensures that when the outside air is introduced through the integrated puncture needle adapter 1 into the vial 600 and the atmospheric pressure is applied inside the vial 600, penetration of bacteria into the vial 600 and the integrated puncture needle adapter 1 can be prevented by the filter member disposed in the filter.

Subsequently, a mouth part 512 of the syringe 500 is connected to the first connecting part 25 of the winged needle 2, after removal of the filter in the case where the filter is mounted. This results in a state wherein the inside of the syringe 500 and the inside of the vial 600 are interconnected through a flow path in the integrated puncture needle adapter 1.

Incidentally, the flow path in the integrated puncture needle adapter 1 means a flow path composed of the inner cavity of the first connecting part 25, the lumen of the tube 24, the inner cavity of the needle hub 22, the lumen of the puncture needle 21, the accommodating space 321, the lumen of the tubular part 343, and the lumen of the hollow needle 349, which are arranged in this order from the side of the syringe 500. The flow path permits transfer of liquid therethrough in both directions.

Incidentally, the assemblage of the integrated puncture needle adapter 1, the connection between the first connecting part 25 and the syringe 500, and the connection between the second connecting part 34 and the vial 600 may not necessarily be conducted in the above-mentioned sequence, and may be conducted in any order or simultaneously.

[3] Next, the pusher 530 in the syringe 500 is pushed and moved distally, whereby the liquid 100 sealed in the syringe 500 is introduced into the vial 600 through the flow path in the integrated puncture needle adapter 1, and the vial 600 is shaken several times. This ensures that the drug 200 in the vial 600 is dissolved or diluted with the liquid 100 flowing into the vial 600, resulting in a state wherein the drug solution 300 is stored in the vial 600.

Figure 6:
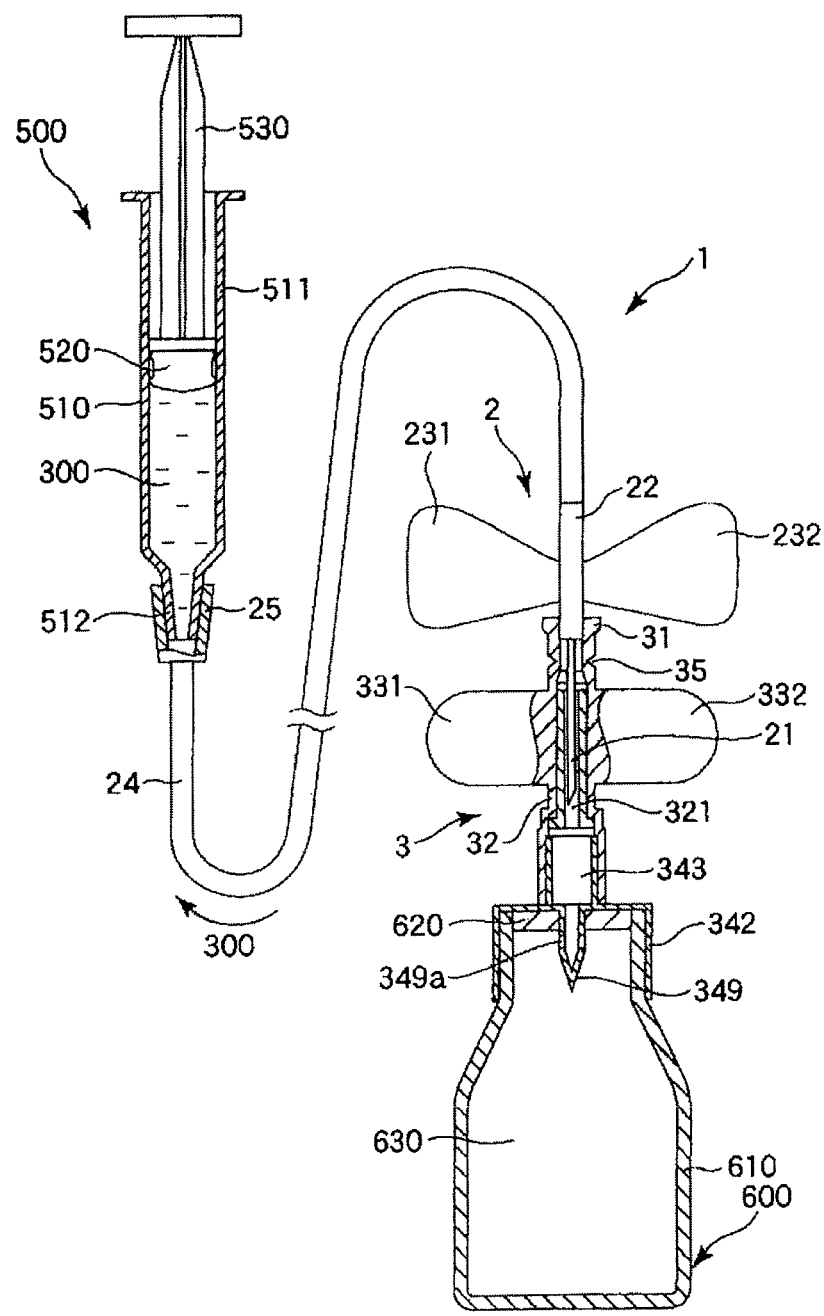
FIG. 6 is a view for illustrating a procedure of using the integrated puncture needle adapter shown in FIG. 1.

[4] Subsequently, the vial 600 is inverted upside down, and the pusher 530 is moved by pulling proximally. By this, as shown in FIG. 6, the drug solution 300 in the vial 600 is sucked from the vial 600 into the syringe 500, to fill the syringe 500.

This step is performed via the flow path in the integrated puncture needle adapter 1. After this step, therefore, a state wherein the flow path is filled with the drug solution 300 is established. Therefore, it is unnecessary to perform priming before the puncture needle 21 is made to puncture the living body, as will be described in procedure [7] later.

[5] Next, the puncture needle accommodating part 32 is gripped by one hand, while the needle hub 22 is gripped by the other hand, and the puncture needle accommodating part 32 and the needle hub 22 are rotated in opposite directions each other to achieve twisting (wrenching) between these members. As a result, the easy-to-break part 351 located between the puncture needle accommodating part 32 and the needle hub 22 is twisted (wrenched) off. Incidentally, in this instance, fingers of the one hand are hooked on the wings 331 and 332 projecting from the puncture needle accommodating part 32, and fingers of the other hand are hooked on the wings 231 and 232 projecting from the needle hub 22, whereby a torque can be applied to the easy-to-break part 351 easily, and the above-mentioned operation can be carried out smoothly.

Figure 7:
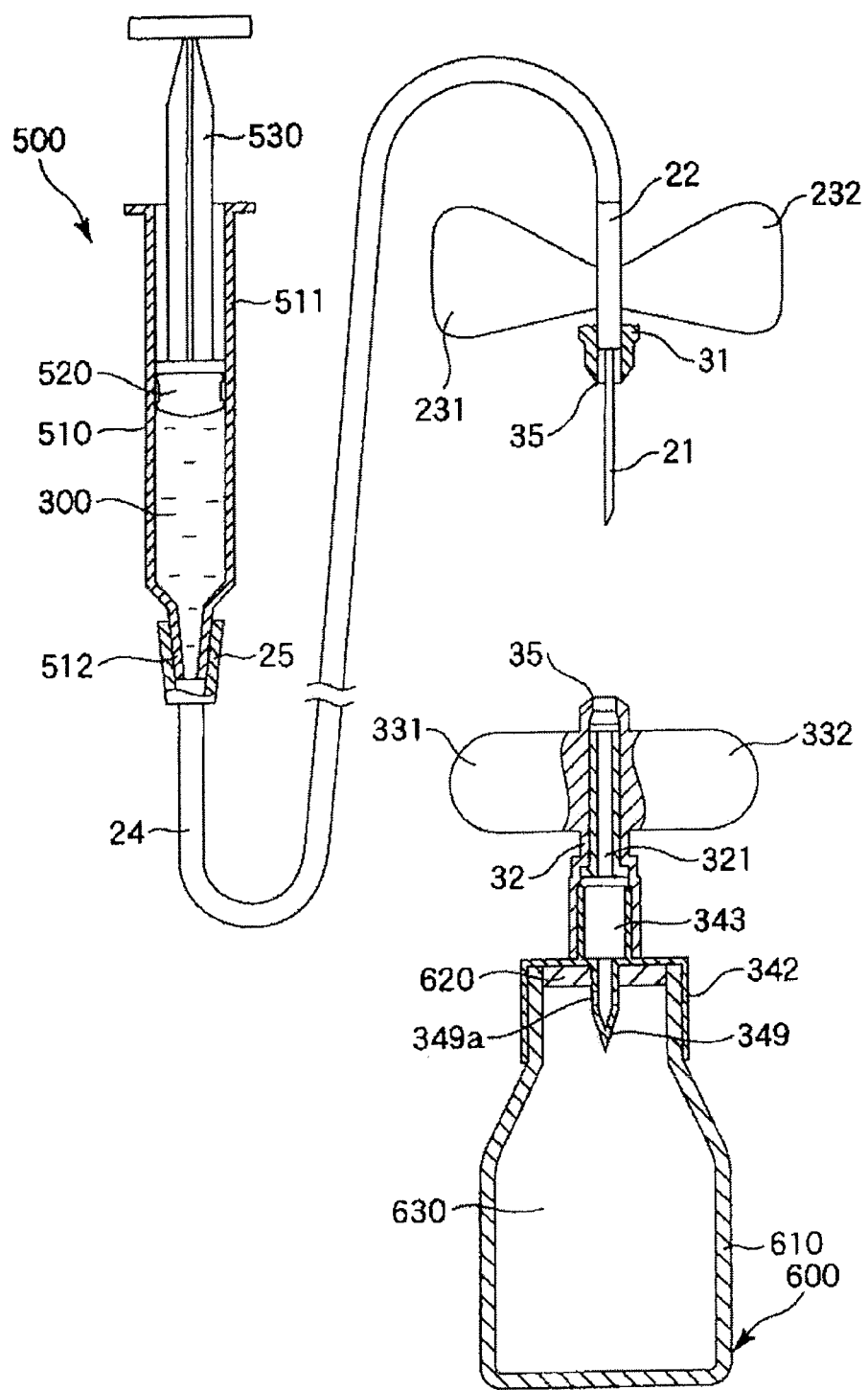
FIG. 7 is a view for illustrating a procedure of using the integrated puncture needle adapter shown in FIG. 1.

[6] Subsequently, that part of the adapter 3 which is located on the distal side relative to the easy-to-break part 351, namely, the puncture needle accommodating part 32 (inclusive of the wings 331 and 332) and the second connecting part 34 are moved distally in the condition where the vial 600 is connected, and the puncture needle 21 is drawn out of the accommodating space 321. As a result, the puncture needle 21 is exposed to the exterior, as shown in FIG. 7.

[7] Next, the needle tip of the puncture needle 21 is made to puncture a target part, and the drug solution 300 in the syringe 500 is administered. In other words, the pusher 530 is moved by pushing distally. As a result, the drug solution 300 in the syringe 500 is discharged from the syringe 500, flows through the tube 24 and the needle hub 22 and then through the puncture needle 21, to be administered.

Figure 8:
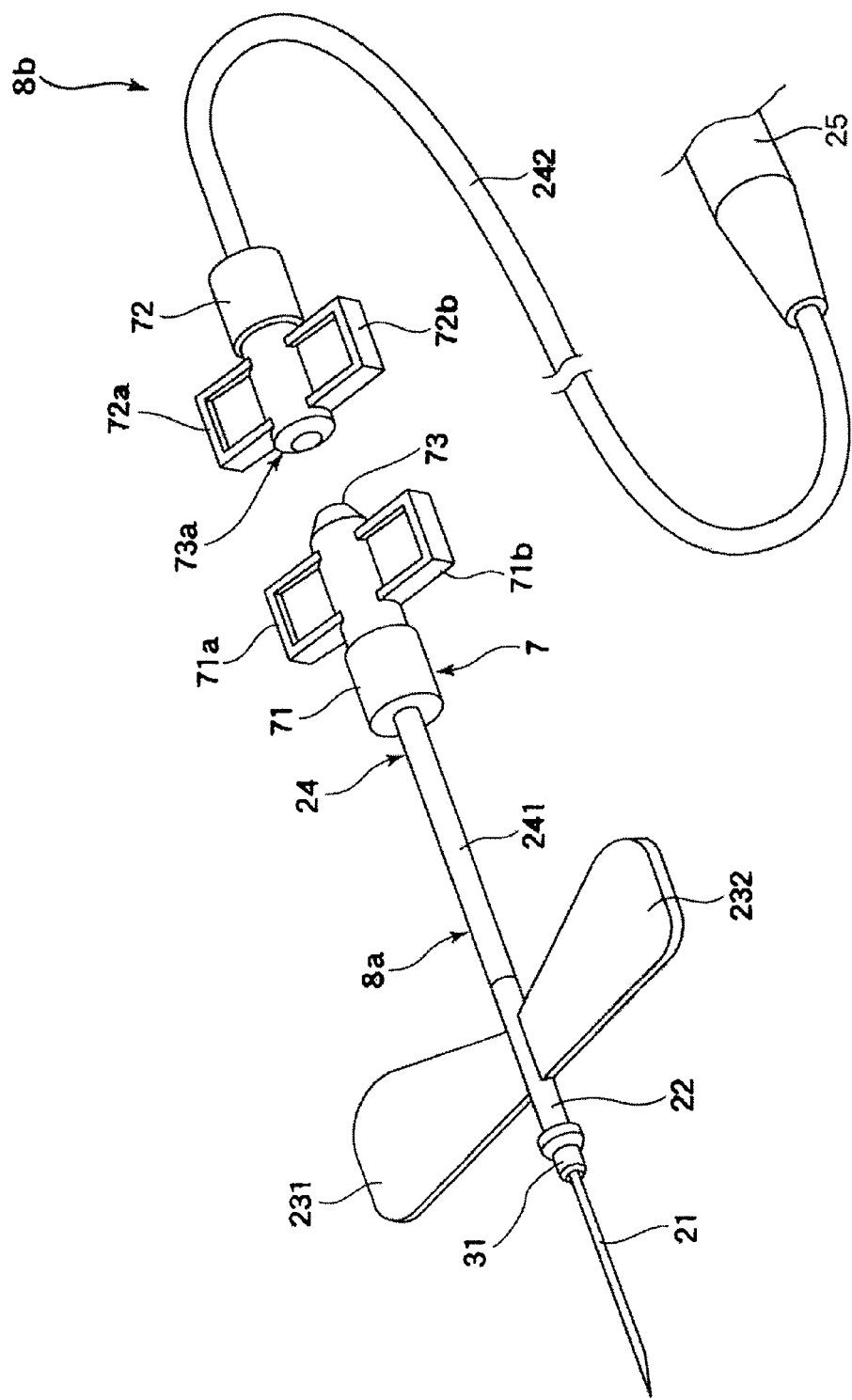
FIG. 8 is a view for illustrating a procedure of using the integrated puncture needle adapter shown in FIG. 1.

After the administration of the drug solution 300 is completed, the puncture needle 21 is drawn out of the target part. Next, the distal portion 71 is gripped by one hand, while the proximal portion 72 is gripped by the other hand, and at least one of the distal portion 71 and the proximal portion 72 is rotated in the manner of twisting it relative to the other, whereby the easy-to-break part 8 located between these portions is twisted (wrenched) off. This results in that the first part 8*a* inclusive of the puncture needle 21 and the second part 8*b* as the rest are separated from each other, as shown in FIG. 8. Then, only the first part 8*a* thus separated is disposed of as the needle waste.

As has been described above, according to the integrated puncture needle adapter 1 (the adapter 3), it is ensured that after the syringe 500 and the vial 600 are individually connected and the drug solution 300 is prepared, a state wherein the living body can be punctured by the puncture needle 21 can be established by only separating the adapter 3 to expose the puncture needle 21. In other words, the state wherein the living body can be punctured by the puncture needle 21 is obtained, without need for a troublesome procedure of detaching a predetermined instrument from the system and attaching another instrument to the system, as in the related art. Accordingly, the integrated puncture needle adapter 1 (the adapter 3) can exhibit excellent operability.

In addition, since parts coming into contact with the liquid 100 or the drug solution 300 are not exposed to the exterior during the above-mentioned procedure, it is possible to securely prevent the contamination of the drug solution 300.

Besides, the priming is conducted simultaneously with the sucking-in of the drug 300 into the syringe 500, in the course of the procedure (in procedure [5]). Therefore, an effort to separately perform the priming can be omitted, so that the operability is enhanced.

In addition, since the puncture needle 21 is exposed finally, safety for the operator can be secured.

Second Embodiment

Now, a second embodiment of the integrated puncture needle adapter of the present invention will be described below.

Figure 9:
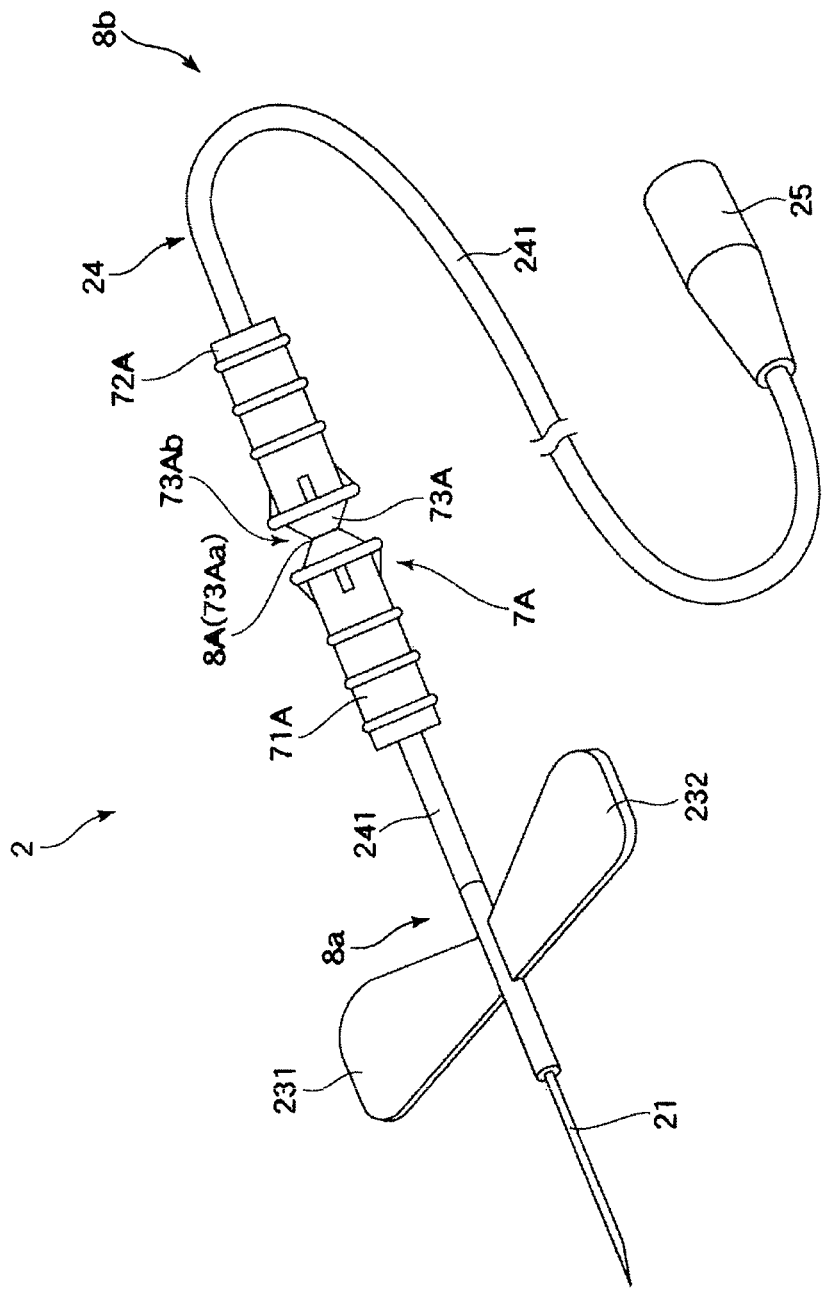
FIG. 9 is a perspective view of a winged needle possessed by a second embodiment of the integrated puncture needle adapter of the present invention.

FIG. 9 is a perspective view of a winged needle possessed by a second embodiment of the integrated puncture needle adapter of the present invention.

While the integrated puncture needle adapter in the present embodiment will now be described below, the following description will be made to center on differences from the integrated puncture needle adapter of the first embodiment above, and the descriptions of the same items as above will be omitted.

The integrated puncture needle adapter in the present embodiment is the same as the integrated puncture needle adapter in the first embodiment above, except for a difference in the configuration of the interconnection member possessed by the tube of the winged needle.

As shown in FIG. 9, an interconnection member 7A in the present embodiment includes a distal portion 71A connected to a distal-side tube 241, a proximal portion 72A connected to a proximal-side tube 242, and an intermediate portion 73A which interconnects the distal portion 71A and the proximal portion 72A. In addition, the intermediate portion 73A has a thin-walled part 73Aa reduced in a wall thickness as compared with the distal portion 71A and the proximal portion 72A. The thin-walled part 73Aa constitutes an easy-to-break part 8A. Incidentally, the thin-walled part 73Aa is formed by forming a groove 73Ab, substantially V-shaped in cross section, in an outer circumference of the intermediate portion 73A over the whole circumference.

The easy-to-break part 8A is broken, for example, by a method wherein the distal portion 71A is gripped by one hand, while the proximal portion 72A is gripped by the other hand, and at least one of these portions is bent relative to the other. According to such a method, the easy-to-break part 8A can be easily broken, and the winged needle 2 can be easily separated into the first part 8a and the second part 8b.

The thin-walled part 73Aa (the easy-to-break part 8A) is preferably formed from a comparatively hard material. This ensures that the strength of the thin-walled part 73Aa can be appropriately enhanced. Consequently, the easy-to-break part 8A can be effectively prevented from undergoing unwilling breakage or unintended breakage, under a force exerted at the time of using the winged needle 2.

The distal portion 71A, the proximal portion 72A, and the intermediate portion 73A are formed integrally. Examples of a material constituting these portions, namely, the material constituting the interconnection member 7A, include various resins such as polyvinyl chloride, polyethylene, polypropylene, cyclic polyolefins such as a cyclic olefin homopolymer (COP) or a cyclic olefin copolymer (COC), polystyrene, polycarbonate, acrylic resins, an acrylonitrile-butadiene-styrene copolymer, polyesters such as polyethylene terephthalate, polyethylene naphthalate, etc., a butadiene-styrene copolymer, and polyamides (e.g., nylon 6, nylon 6-6, nylon 6-10, nylon 12).

While the integrated puncture needle adapter of the present invention has been described based on the embodiments shown in the drawings, the invention is not to be restricted to the embodiments, and the configurations of the components can be replaced by components of arbitrary configurations having the same or equivalent functions. Besides, arbitrary components or structures may be added to the present invention.

In addition, while a mode wherein the separable part is composed of an easy-to-break part made to be thinner and more brittle has been described in the embodiments above, the configuration of the separable part is not specifically restricted, insofar as the part on the distal side of the separable part and the part on the proximal side of the separable part can be separated from each other. For instance, a soft part formed from a material softer as compared with the puncture needle accommodating part and the tubular fixing part may be formed between these parts, and the soft part may be used as the separable part.

Besides, while a mode wherein the separable part is formed between the puncture needle accommodating part and the tubular fixing part has been described in the embodiments above, the position where to form the separable part is not specifically restricted, insofar as the puncture needle can be exposed. For instance, the separable part may be formed at an intermediate portion of the tubular fixing part (at such a position as not to overlap with the needle hub), or may be formed at an intermediate portion of the puncture needle accommodating part.

In addition, while the configuration wherein the integrated puncture needle adapter is built up by combining the adapter and the winged needle has been described in the embodiments above, this is not restrictive of the configuration of the integrated puncture needle adapter. For instance, a combination of an adapter with an injection needle wherein a needle hub and a first connecting part are integrally formed without any tube therebetween may be used to configure the integrated puncture needle adapter.

Besides, while the syringe is used as the liquid storage container and the vial is used as the drug storage container in the embodiments above, the liquid storage container and the drug storage container are not specifically restricted. For instance, soft or flexible containers such as infusion bags and the like may be used as the storage containers.

In addition, in the second embodiment above, the configuration has been described in which the groove substantially V-shaped in cross section is formed in the outer circumference of the intermediate portion of the interconnection member over the whole circumference, whereby the thin-walled part (easy-to-break part) is provided over the whole circumference of the intermediate portion. However, the thin-walled part may not necessarily be formed over the whole circumference but may be formed at only a part of the circumference of the intermediate portion. This configuration ensures that the easy-to-break part cannot be broken unless the distal portion and the proximal portion are bent according to the portion where the thin-walled part is formed. In other words, the easy-to-break part can thereby be more effectively prevented from undergoing unwilling breakage.

Besides, while a mode wherein the tube is separated into the distal-side tube and the proximal-side tube has been described in the embodiments above, this is not restrictive of the configuration of the tube. For instance, the tube may be composed of a non-separated single tube. In other words, the distal-side tube and the proximal-side tube may be integrally formed. In this case, the interconnection member does not have any thin-walled part, the distal portion and the proximal portion are formed as separate bodies, and these portions are fixed juxtaposedly with the tube by, for example, adhesion with an adhesive. The tube itself corresponding to the position between the distal portion and the proximal portion constitutes the easy-to-break part. In such a configuration, the easy-to-break part can be twisted (wrenched) off, namely the tube itself can be broken, for example, by a method wherein the distal portion is gripped by one hand, while the proximal portion is gripped by the other hand, and at least one of the distal portion and the proximal portion is rotated in the manner of twisting (wrenching) it relative to the other. As a result, the puncture needle assembly can be separated into a first part and a second part. Incidentally, the distal portion and the proximal portion are preferably fixed to the tube, with some gap therebetween, in order that the easy-to-break part can be easily deformed at the time of twisting (wrenching) off the easy-to-break part.

INDUSTRIAL APPLICABILITY

According to the present invention, the state wherein the living body can be punctured by the puncture needle can be established, by only exposing the puncture needle through separating the part on the distal side of the separable part from the part on the proximal side of the separable part, starting from the state wherein the drug storage container is connected to the second connecting part. In other words, the state wherein the living body can be punctured by the puncture needle is obtained, without need for the troublesome procedure of detaching the predetermined instrument from the system and attaching another instrument to the system, during use of the system, as in the related art. Therefore, the excellent operability can be exhibited.

In addition, the parts coming into contact with the drug solution to be administered into the living body are not exposed to the exterior during the using procedure. Therefore, the contamination of the drug solution can be securely prevented from occurring. Besides, the priming for the drug solution is conducted during the using procedure. Therefore, an effort to separately perform the priming can be omitted, which also promises the enhanced operability. Further, since the puncture needle is exposed finally, safety for the operator is ensured.

Thus, the integrated puncture needle adapter of the present invention has industrial applicability.

The invention claimed is:

1. An integrated puncture needle adapter for connecting a drug storage container having a drug storage space that stores a drug and a liquid storage container having a liquid storage space that stores a liquid for dissolving or diluting the drug, the integrated puncture needle adapter comprising:
    a puncture needle having a needle tip capable of puncturing a living body at a distal end of the puncture needle and an internal passage opening at both ends of the puncture needle;
    a needle hub which supports the puncture needle so that the needle tip of the puncture needle protrudes from a distal side of the needle hub;
    a first connecting part which is provided on a proximal side of the needle hub, and which connects the liquid storage space and the internal passage in a liquid-tight manner by a connection with the liquid storage container;
    a tubular fixing part which is provided on the distal side of the needle hub, and which is permanently fixed to the needle hub in a liquid tight manner;
    a tubular puncture needle accommodating part which is provided on a distal side of the tubular fixing part integrally with the tubular fixing part, and wherein the tubular puncture needle accommodating part has therein an accommodating space for accommodating the puncture needle and a diameter of the accommodating space is greater by 0.2 to 5 mm than an outside diameter of the puncture needle;
    a second connecting part which is provided on a distal side of the puncture needle accommodating part so as to communicate with the accommodating space, and wherein the second connecting part connects the drug storage space and the internal passage in a liquid-tight manner by a connection with the drug storage container; and
    a separable part is provided between the tubular fixing part and the puncture needle accommodating part, wherein the separable part is capable of separating a distal part at a distal side relative to the separable part from a proximal part at a proximal side relative to the separable part, and the puncture needle is exposed when separated.

2. The integrated puncture needle adapter according to claim 1, wherein
    the liquid storage container is a syringe; and
    the integrated puncture needle adapter is used by, in a state where the drug storage container is connected to the second connecting part and the syringe is connected to the first connecting part,
        transferring the liquid into the drug storage space through the puncture needle, the accommodating space and the second connecting part by an operation of the syringe to obtain a drug solution as a mixture of the liquid with the drug,
        sucking the drug solution into the syringe through the second connecting part, the accommodating space and the puncture needle by the operation of the syringe, and
        separating the distal part at the distal side relative to the separable part together with the drug storage container from the proximal part at the proximal side relative to the separable part, thereby exposing the puncture needle.

3. The integrated puncture needle adapter according to claim 1, wherein the separable part comprises an easy-to-break part which is easier to break than parts other than the separable part.

4. The integrated puncture needle adapter according to claim 3, wherein the easy-to-break part is broken by rotating at least one of a distal part at a distal side relative to the easy-to-break part and a proximal part at a proximal side relative to the easy-to-break part in a circumferential direction in relation to the other.

5. The integrated puncture needle adapter according to claim 1, wherein the puncture needle accommodating part is provided with a projection which projects outwardly with respect to the accommodation space.

6. The integrated puncture needle adapter according to claim 1, wherein the needle hub is provided with a projection which projects outwardly with respect to a body of the needle hub.

7. The integrated puncture needle adapter according to claim 1, wherein the tubular fixing part is permanently fixed to the needle hub by welding, or by an adhesive or by a combination of welding and an adhesive.

8. An integrated puncture needle adapter for connecting a drug storage container having a drug storage space that stores a drug and a liquid storage container having a liquid storage space that stores a liquid for dissolving or diluting the drug, the integrated puncture needle adapter comprising:
    a puncture needle having a needle tip capable of puncturing a living body at a distal end of the puncture needle and an internal passage opening at both ends of the puncture needle;
    a needle hub which supports the puncture needle so that the needle tip of the puncture needle protrudes from a distal side of the needle hub;
    a first connector which is provided on a proximal side of the needle hub, and which connects the liquid storage space and the internal passage in a liquid-tight manner by a connection with the liquid storage container;
    a tubular fixing part which is provided on the distal side of the needle hub, and which is permanently fixed to the needle hub in a liquid-tight manner;
    a tubular puncture needle receiver which is provided on a distal side of the tubular fixing part integrally with the tubular fixing part, wherein the tubular puncture needle receiver has therein a receiving space for accommodating the puncture needle;
    a second connector which is provided on a distal side of the puncture needle receiver so as to communicate with the receiving space, and wherein the second connector connects the drug storage space and the internal passage in a liquid-tight manner by a connection with the drug storage container; and
    a separable part provided between the tubular fixing part and the puncture needle receiver, wherein the separable part is capable of separating a distal part at a distal side relative to the separable part from a proximal part at a proximal side relative to the separable part, and the puncture needle is exposed when the distal part and the proximal part are separated.

9. The integrated puncture needle adapter according to claim 8, wherein
    the liquid storage container is a syringe; and the integrated puncture needle adapter, when the drug storage container is connected to the second connecting part and the syringe is connected to the first connecting part is operative to, transfer the liquid into the drug storage space through the puncture needle, the receiving space and the second connecting part by an operation of the syringe to obtain a drug solution as a mixture of the liquid with the drug, suck the drug solution into the syringe through the second connecting part, the receiving space and the puncture needle by operation of the syringe, and separate the distal part at the distal side relative to the separable part together with the drug storage container from the proximal part at the proximal side relative to the separable part, thereby exposing the puncture needle.

10. The integrated puncture needle adapter according to claim 8, wherein the separable part comprises an easy-to-break part which is easier to break than parts other than the separable part.

11. The integrated puncture needle adapter according to claim 10, wherein the easy-to-break part is broken by rotating at least one of a distal part at a distal side relative to the easy-to-break part and a proximal part at a proximal side relative to the easy-to-break part in a circumferential direction in relation to the other.

12. The integrated puncture needle adapter according to claim 8, wherein the puncture needle receiver is provided with a projection which projects outwardly with respect to the receiving space.

13. The integrated puncture needle adapter according to claim 8, wherein the needle hub is provided with a projection which project outwardly with respect to a body of the needle hub.

14. The integrated puncture needle adapter according to claim 8, wherein the tubular fixing part is permanently fixed to the needle hub by welding, or by an adhesive or by a combination of welding and an adhesive.

* * * * *